(12) United States Patent
Jolivet-Reynaud et al.

(10) Patent No.: US 6,602,853 B1
(45) Date of Patent: Aug. 5, 2003

(54) ANTIGENIC PEPTIDES REACTING WITH ANTI-OVARY ANTIBODIES

(75) Inventors: Colette Jolivet-Reynaud, Bron (FR); Gilbert Faure, Nancy (FR); Pascal Dalbon, Lyons (FR); Michel Jolivet, Bron (FR); Marie-Christine Bene, Nancy (FR)

(73) Assignee: Bio Merieux, Marcy l'Etoile (FR)

( * ) Notice: Subject to any disclaimer, the term of this patent is extended or adjusted under 35 U.S.C. 154(b) by 0 days.

(21) Appl. No.: 09/331,872

(22) PCT Filed: Dec. 31, 1997

(86) PCT No.: PCT/IB97/01611

§ 371 (c)(1),
(2), (4) Date: Sep. 24, 1999

(87) PCT Pub. No.: WO98/29450

PCT Pub. Date: Jul. 9, 1998

(30) Foreign Application Priority Data

Dec. 31, 1996 (FR) .............................................. 96 16385

(51) Int. Cl.$^7$ .............................................. A61K 38/00
(52) U.S. Cl. ........................................ 514/13; 530/326
(58) Field of Search ................................ 530/326, 327, 530/328; 514/13, 14, 15, 16

(56) References Cited

PUBLICATIONS

Ngo et al. The Protein Folding Problem and Tertiary Structure Prediction, 1994, Merg et al., Birkhauser, Boston, pp. 433 & 492–495, 1994.*

Colman et al. Research in Immunology: vol. 145: 33–36, 1994.*

Santa–Coloma, Tomas A. et al., "Serine Analogues of hFSH– BETS–(33–53) and hFSH–BETA–(81–95) Inhibit hFSH Binding to Receptor," Biochemical and Biophysical Research Communications, vol. 184, No. 3, 1992, pp. 1273–1279.

Saxena, Brij B. et al., "Chemical Synthesis of Peptide Fragments of the Hormone–Specific β–Subunit of Human Follicle–Stimulating Hormone," Biochemistry, vol. 25, No. 3, 1985, pp. 813–816.

Santa–Coloma, Tomas A. et al., "A Synthetic Peptide Encompassing Two Discontinuous Regions of hFSH–.beta. Subunit Mimics the Receptor Binding Surface of the Hormone," Abstract only No. XP 002040736.

Cameron, I.T. et al., "Occult*Ovarian*Failure: A Syndrome of Infertility, Regular Menses, and Elevated Follicle–Stimulating Hormone Concentration," Abstract only No. XP 002040733.

Tang, V.W., et al., "Premature*Ovarian*Failure: A Search for Circulating Factors Against Gonadotropin Receptors," Abstract only No. XP 002040734.

Baarbarino–Monnier, P. et al., "Ovarian Autoimmunity and Corticotherapy in an In–Vitro Fertilization Attempt,," Abstract only No. XP 002040735.

* cited by examiner

*Primary Examiner*—Patrick J. Nolan
(74) *Attorney, Agent, or Firm*—Oliff & Berridge, PLC

(57) ABSTRACT

Oligopeptides containing one of SEQ ID NOs: 1–5 may be used as antigenic compounds to recognize anti-ovary antibodies. The oligopeptides may also be used as immunogenic compounds to induce the production of anti-ovary antibodies.

3 Claims, 4 Drawing Sheets

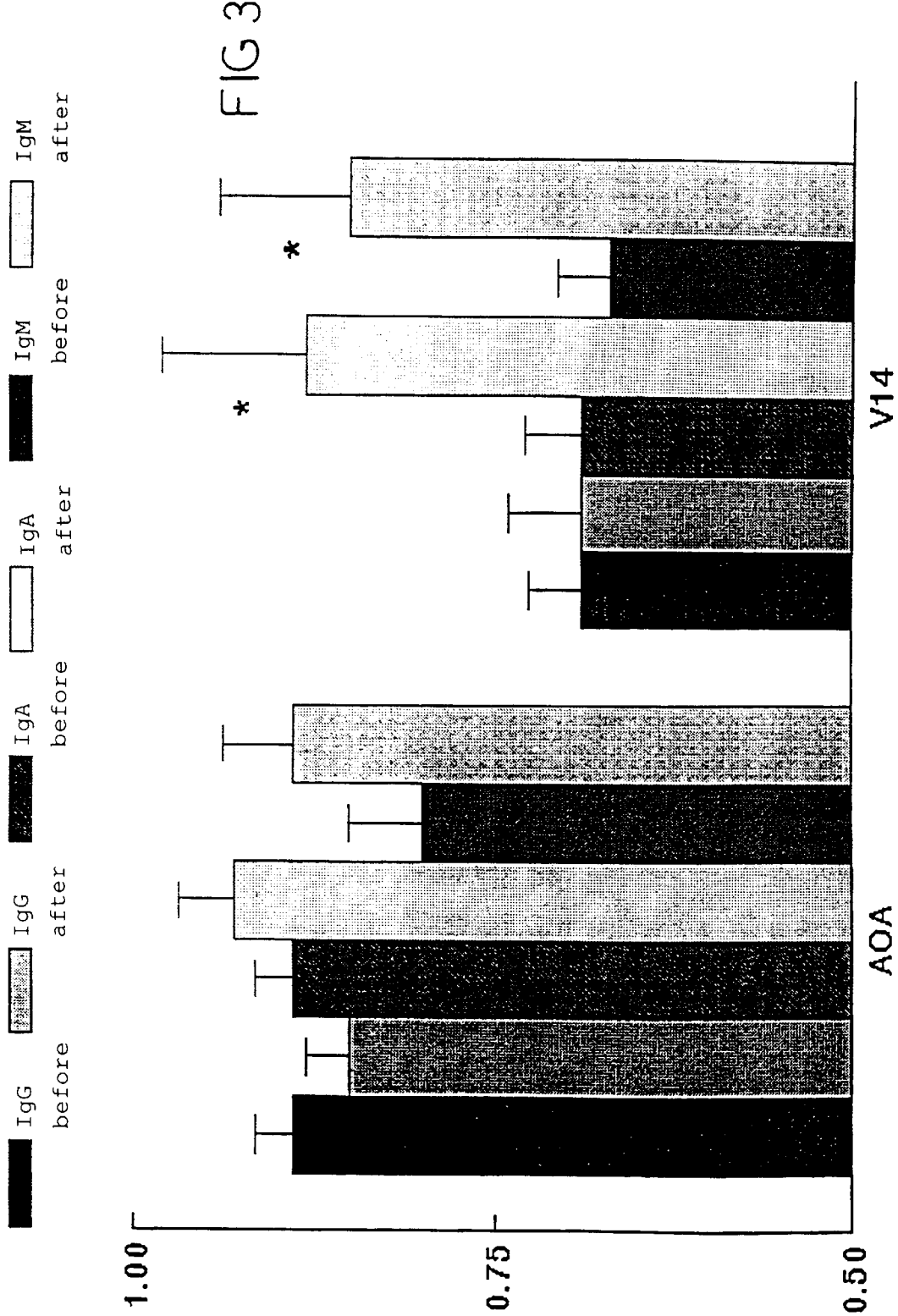

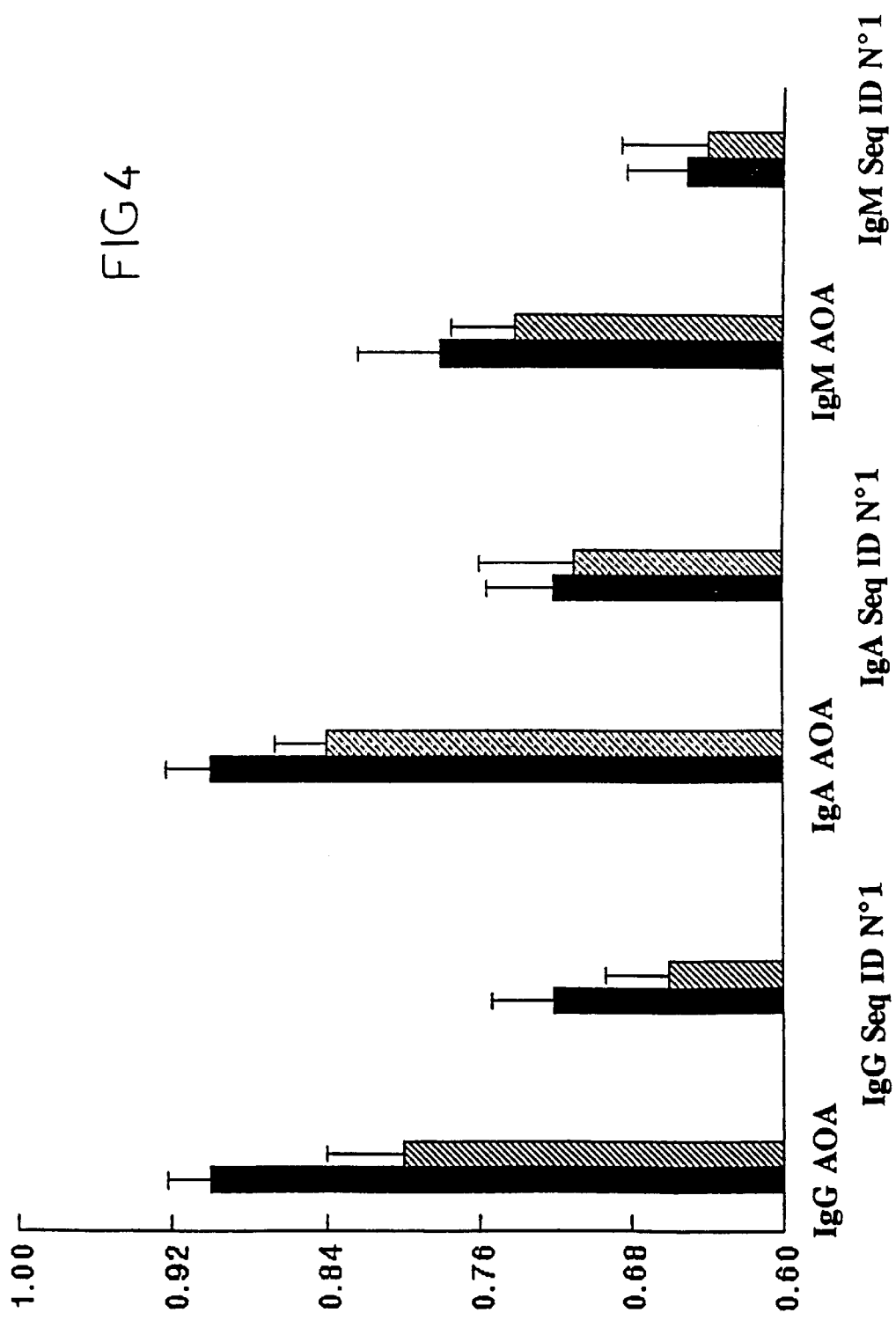

ANTIGENIC PEPTIDES REACTING WITH ANTI-OVARY ANTIBODIES

Figure 1:
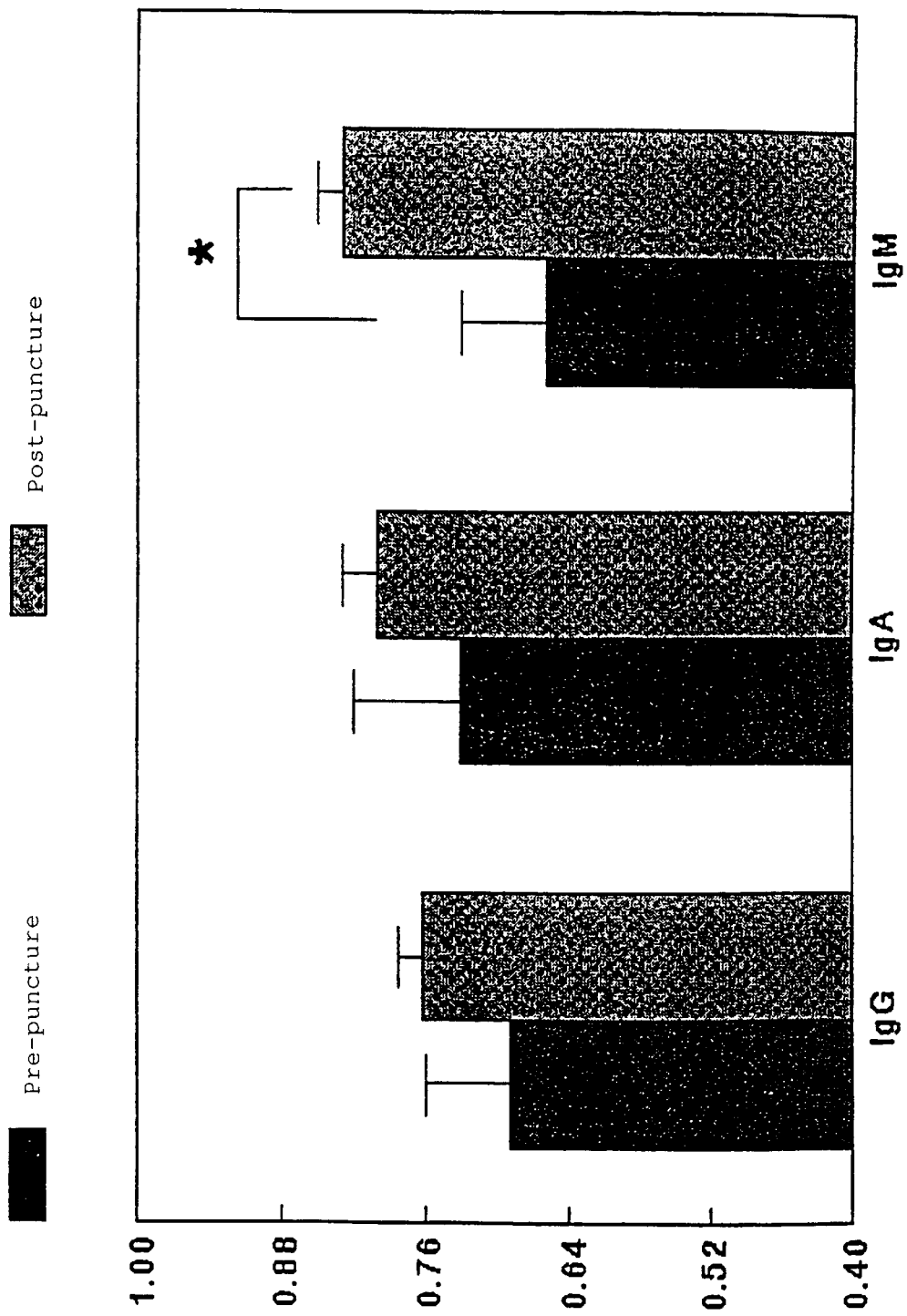

This application is a national stage application of PCT/IB97/01611 filed Dec. 31, 1997.

The present invention concerns immunology and its direct impact in endocrinology, both in man and in animals. More particularly, this impact concerns the reproductive system. It is in fact through pathologies such as repeated spontaneous abortions, antiphospholipid antibody syndrome and preeclampsia that dysimmune mechanisms have been observed in gynaecology and obstetrics.

The development of in vitro fertilization (IVF) techniques has greatly contributed to improving understanding of the mechanisms of human fertilization. However, this technique sometimes encounters unexpected failures. Involvement of unfavorable immune reactions generated by the technique itself has been envisaged, on account of the considerable traumas inflicted on the ovary in the course of the hormonal stimulation and follicular punctures, which can liberate substantial quantities of potentially antigenic material into the peritoneal cavity.

Previous studies have revealed antigenic components in the thecae, constituents of the ovary, and the presence of serum antibodies directed against the cells of the ovarian thecae or against the corpus luteum has been reported in different pathological contexts (adrenal insufficiency, ovarian insufficiency, to a greater or lesser extent associated with polyendocrinopathy) (6). Furthermore, SHIVERS et al. (1) have shown that antibodies produced against ovarian antibodies, called anti-ovary antibodies (AOA) inhibited in vitro fertilization in the hamster.

The publication by SAXENA and RATHNAM ("Chemical synthesis of peptide fragments of, the hormone-specific beta-subunit of human follicle stimulating hormone", *Biochemistry*, Vol.24, No.3, 1985, pp 813–816) discloses the chemical synthesis of peptides in order to determine the specific antigenic determinants of the human FSH hormone. These are the peptides V3+½ C2 (corresponding to the amino acids 76–118 of the β-subunit of FSH) and V1+C1 (corresponding to the amino acids 1–33 of the β-subunit of FSH) which are presented as being the antigenic determinants of the hormone FSH which are reactive toward antibodies to the hormones LH and TSH, which proves a homology of the antigenic sites for the three hormones FSH, LH and TSH.

The publication by SANTA-COLOMA et al. ("Serine analogues of hFSH-beta-(33–53) and hFSH-beta-(81–95) inhibit hFSH binding to receptor", *Biochemical and Biophysical Research Communications*, Vol.184, No.3, May 15, 1992, pp 1273–1279) discloses synthetic peptides corresponding to the amino acids 33–53 and 81–95 of the β-subunit of FSH, containing free sulfydryl groups, which make it possible to inhibit the binding of the hormone FSH to its receptor and which also display a partial agonist activity on the said FSH receptor. It is stated that the 4 cysteine residues are not essential to the binding to the receptor but are important for the partial agonist activity of these peptides on the receptor.

The publication by TANG et al. ("Premature ovarian failure: a search for circulating factors against gonadotrophin receptors, *American Journal of Obstetrics and Gynecology*, Vol.146, No.7, Aug. 1, 1983, pp 813–821) presents a study performed on nine patients displaying early menopause. This study suggests that factors active against the gonadotrophin receptor seem not to be involved in the majority of patients displaying premature failure of the ovaries. Instead, a factor active against the FSH receptor, which may be an antibody, is suggested as being possibly present in patients displaying early menopause and auto-immunity.

The inventors of the present invention have surprisingly discovered that a well defined peptide sequence, which corresponds in its primary structure to a part of the β-subunit of FSH, displayed an antigenic and immunogenic character toward anti-ovary antibodies such as previously defined.

In the course of previous studies, the authors of the present invention demonstrated the existence of a correlation between the level of anti-ovary antibodies observed and the failures of IVF attempts (2).

The authors then became interested in the antigens potentially involved in the generation of these auto-immune responses, and firstly isolated and characterized an immunodominant peptide reacting with the anti-ovary antibodies, then demonstrated the value of this peptide in the detection of AOAs.

The importance of this detection has been demonstrated, in different pathologies resulting in sterility, by the authors of the present invention.

In examining the AOA levels before and after follicular puncture, they observed, in women undergoing a first IVF attempt, a level of AOA higher than the level in control women, even when for these women an IVF protocol had been recommended for different types of sterility, namely sterility of tubal origin, of idiopathic origin, resulting from endometriosis or linked with severe ovulation disorders.

The detection of anti-ovary antibodies in a sterility pathology, after one or several vain IVF attempts, can become decisive to the policy to be followed concerning these failures. The authors have in fact demonstrated the efficacy of corticotherapy on the favorable outcome of an IVF attempt (3).

The study of ovarian auto-immunity is nowadays essentially addressed using animal tissue substrates or animal ovarian extracts (4). The ovarian extract used by MONCAYO et al. was of animal, namely bovine, origin. It has not been demonstrated that the antigens recognized were actually the same in the human species and in cattle.

According to the present invention, an antigenic peptide capable of replacing ovarian extracts, and follicle stimulating hormone (FSH or gonadotrophin A) which remains a product difficult to purify, and only on the market in recombinant forms, is provided.

The immunochemical studies performed by the authors have thus made it possible to detect an oligopeptide immunodominant toward the AOAs, belonging to the β-chain of FSH.

Thus, the first object of the invention is an oligopeptide consisting of the reference peptide sequence Thr Gln Cys His Cys Gly Lys Cys (SEQ ID NO: 5), or any peptide sequence, functional variant of the said reference sequence, in the sense that the first displays an antigenicity, and/or an immunogenicity toward anti-ovary antibodies equivalent to the antigenicity and/or the immunogenicity of the second.

A functional variant of the said reference sequence is advantageously obtained by modifying the hydrocarbon residue of at least one of the amino acids of the said reference sequence, while conserving an antigenicity identical or similar to that of the said reference sequence, or else by modifying the hydrocarbon residue of at least one of the amino acids of the said reference sequence, while substantially retaining the hydrophilic/hydrophobic character of the said hydrocarbon residue.

By equivalent activity is understood an identical or similar antigenic and/or immunogenic activity, even if differences of degree may exist in the antigenic and/or immunogenic responses.

An oligopeptide of the invention can thus consist of a peptide sequence corresponding to the formula:

Xaa1-Xaa2-Xaa3-Xaa4-Xaa5-Xaa6-Xaa7-Xaa8, in which formula:
Xaa1 represents threonine,
Xaa2 represents glutamine,
Xaa3 represents cysteine,
Xaa4 represents histidine,
Xaa5 represents cysteine,
Xaa6 represents glycine,
Xaa7 represents lysine, and
Xaa8 represents cysteine,
the said sequence being identified by SEQ ID NO: 5, or a peptide sequence which is a functional variant of SEQ ID NO: 5.

Preferably, the said functional variant sequence corresponds to the formula

Xaa1-Xaa2-Xaa3-Xaa4-Xaa5-Xaa6-Xaa7-Xaa8, in which formula:
Xaa1 represents threonine or the unit $NH_2$—$CH(R1)$ COOH where R1 is an oxygenated hydrocarbon radical conferring on the said variant sequence an antigenicity identical or similar to that of SEQ ID NO: 5,
Xaa2 represents glutamine or the unit $NH_2$—$CH(R2)$ COOH where R2 is an oxygenated and/or aminated hydrocarbon radical conferring on the said variant sequence an antigenicity identical or similar to that of SEQ ID NO: 5,
Xaa3 represents cysteine or the unit $NH_2$—$CH(R3)$ COOH where R3 is a sulfurated hydrocarbon radical conferring on the said variant sequence an antigenicity identical or similar to that of SEQ ID NO: 5,
Xaa4 represents histidine or the unit $NH_2$—$CH(R4)$ COOH where R4 is an aminated hydrocarbon radical conferring on the said variant sequence an antigenicity identical or similar to that of SEQ ID NO: 5,
Xaa5 represents cysteine or the unit $NH_2$—$CH(R5)$ COOH where R5 is a sulfurated hydrocarbon radical conferring on the said variant sequence an antigenicity identical or similar to that of SEQ ID NO: 5,
Xaa6 represents glycine or the unit $NH_2$—$CH(R6)COOH$ where R6 is a hydrocarbon radical conferring on the said variant sequence an antigenicity identical or similar to that of SEQ ID NO: 5,
Xaa7 represents lysine or the unit $NH_2$—$CH(R7)COOH$ where R7 is an aminated hydrocarbon radical conferring on the said variant sequence an antigenicity identical or similar to that of SEQ ID NO: 5,
Xaa8 represents cysteine or the unit $NH_2$—$CH(R8)$ COOH where R8 is a sulfurated hydrocarbon radical conferring on the said variant sequence an antigenicity identical or similar to that of SEQ ID NO: 5.

Advantageously, the constituent radicals R1 and/or R2 and/or R3 and/or R4 and/or R5 and/or R6 and/or R7 and/or R8 of the said units are respectively selected among radicals conferring on the said units a hydrophilicity/hydrophobicity identical or similar to that of the respectively corresponding amino acids.

It is evident from the general knowledge of the person skilled in immunology and peptide synthesis that the hydrophilic/hydrophobic character of the constituent units of proteins/peptides is of importance to the antigenic power of the latter. Moreover, many works on general biochemistry (5) have classified the 20 amino acids on the basis of their greater or lesser hydrophobic/hydrophilic character. According to the present invention, it is considered that the selection of the radicals R1 to R8 in the above formula can be made by the aforesaid skilled person with the aid of the said works, and that he in addition has routine experimental protocols available for determining the hydrophilic/hydrophobic character of the constituent unit-that he has selected.

Of course, other physicochemical parameters of the amino acids can be used to determine variant sequences, such as for example the pKa constant.

As functional variants of the peptide sequence SEQ ID No.5, the oligopeptide consisting of the peptide sequence SEQ ID No.1 for example, may be cited. Example 2 below in fact demonstrates identical activity for the oligopeptides SEQ ID No.1 and 5. The oligopeptides SEQ ID No.2, 3 and 4, having weaker activity than the oligopeptides cited above, are considered in the present invention as functional variants. In fact, inasmuch as their antigenic or immunogenic activity toward anti-ovary antibodies is weaker, but useful all the same, for example mixed with other oligopeptides of the same activity, in a diagnostic kit, these oligopeptides are functional variants of SEQ ID No.5.

The oligopeptides described at the end of the specification are:

SEQ ID No.1: linear sequence of 16 amino acids corresponding to the sequence of amino acids 78–93 of the β-chain of FSH, SEQ ID No.2: sequence of 16 amino acids, bridged by a disulfide bond in position 5 and 7, corresponding to the sequence of amino acids 78–93 of the β-chain of FSH, SEQ ID No.3: sequence of 16 amino acids, bridged by a disulfide bond in position 5 and 10, corresponding to the sequence of amino acids 78–93 of the β-chain of FSH, SEQ ID No.4: sequence of 16 amino acids, bridged by a disulfide bond in position 7 and 10, corresponding to the sequence of amino acids 78–93 of the β-chain of FSH, SEQ ID No.5: linear sequence of 8 amino acids corresponding to the sequence of amino acids 80–87 of the β-chain of FSH.

The surprising feature of the invention is that the oligopeptides of the invention, such as those represented by SEQ ID No.1 and 5, the primary amino acid structure of which corresponds respectively to the amino acids 78–93 and 80–87 of the β-chain of FSH, although probably having a three-dimensional structure different from that of the β-chain of FSH, display an antigenic and/or immunogenic activity toward anti-ovary antibodies.

In a preferred mode of implementation according to the invention, the oligopeptide has the peptide sequence identified by SEQ ID No.5.

In another preferred mode of implementation according to the invention, the oligopeptide has the peptide sequence identified by SEQ ID No.1.

In yet another mode of implementation according to the invention, the oligopeptide has the peptide sequence identified by SEQ ID No.2 or 3 or 4, as identified at the end of the specification.

A second object of the present invention is an antigenic compound capable of being recognized by the anti-ovary antibodies, or an immunogenic compound capable of inducing the production of anti-ovary antibodies, the said compound corresponding to any one at least of the following definitions:

- a compound having a peptide sequence including the sequence of the oligopeptide described above, and preferably including the sequence SEQ ID No.5; in particular, such a compound has a peptide sequence which includes or which consists of SEQ ID No.1, as identified at the end of the specification;
- a compound consisting of FSH or a functional variant of FSH;
- a compound consisting of the β-chain of FSH;
- a compound whose antigenicity or immunogenicity is representative of the anti-genicity or immunogenicity of the crude ovarian antigens, the primary structure of the said compound including a peptide sequence corresponding to the sequence of amino acids 78–93 of the β-chain of the FSH of the human race or of any animal species, the said sequence being immunodominant and being recognized by the anti-ovary antibodies of the said human race or of the said species.

Another object of the invention is a composition antigenic or immunogenic toward anti-ovary antibodies, including an antigenic or immunogenic compound such as defined above.

One application of an oligopeptide or of a compound of the invention lies in the detection and/or quantification of anti-ovary antibodies. Thus a third object of the invention is a process for detection and/or quantification of anti-ovary antibodies in a biological sample, including the stage consisting in placing the said biological sample in contact with at least one peptide or one compound of the invention, and in observing the formation of an antigen-antibody complex between the said peptide or compound and an anti-ovary antibody.

The formation of the aforesaid complex can be detected by different classical bioassay formats, known to the skilled person, such as immunocytochemical and immunoenzymatic (ELISA) techniques, competition techniques and "sandwich" techniques.

In accordance with this process, the biological sample is advantageously selected among the blood serum, the follicular liquid, the peritoneal liquid, the cervical mucus and the saliva.

The stage of observation of the formation of an antigen-antibody complex is preferably effected by the immunoenzymatic technique called ELISA, with which it has been possible to obtain results perfectly correlated with those obtained by the reference technique for the skilled person, namely indirect immunofluorescence.

Finally, the last objects of the invention are firstly a reagent for detection and/or quantification of anti-ovary antibodies including at least one peptide or one compound of the invention, and secondly a kit for detection and/or quantification of anti-ovary antibodies including at least the said reagent.

Before presenting the benefits of the invention and describing it in more detail, certain terms used in the present text are defined below.

A peptide sequence, functional variant of the reference peptide sequence (SEQ ID NO: 5) is a sequence of amino acids, called modified, differing from the sequence (SEQ ID NO: 5) by modifications which confer on the said functional variant sequence an antigenicity identical or similar to that of the reference sequence. The modifications of the said sequence can concern its size, and each of the amino acids that constitute it. Such modifications are in particular selected among substitutions, deletions and additions of amino acids in the sequence of the first oligopeptide, but also among replacement of an amino acid of the L series by an amino acid of the D series, modification of the side-chains of the amino acids, modification of the peptide bonds such as carba, retro, inverso, retro-inverso, reduced or methylene-oxy bonds, subject to the condition that these modifications do not result in any significant alteration of the antigenic properties of the said sequence toward anti-ovary antibodies.

As an example of substitution, and as previously mentioned, an amino acid of SEQ ID No: 5 can be replaced by another amino acid of the same hydrophilicity/hydrophobicity or of comparable hydrophilicity/hydrophobicity.

The competent skilled person, who routinely utilizes the techniques at his disposal, in particular the techniques of automated peptide synthesis and the techniques of determination of the antigenicity of a peptide such as ELISA tests, is capable, in a first stage, of synthesizing a modified sequence such as defined above, and, in a second stage, of testing the antigenicity of the peptide obtained. If the latter displays an antigenicity at least substantially equivalent to that of the said reference sequence, it corresponds to the definition of functional variant sequence of the said reference sequence. The skilled person can in particular refer to the examples 2 and 3 below, which describe a protocol to be followed for comparing the antigenicity of two peptides toward AOAs.

A compound of the invention includes a sequence of a variable number of amino acids, including at least the sequence of one oligopeptide of the invention. It can in particular consist of a protein, a glycoprotein, a fusion protein or a fusion peptide. It can moreover be bound on a solid support.

An oligopeptide or a polypeptide of the invention may be obtained by any obtention route and in particular chemical synthesis or genetic recombination.

The objects of the invention are also of value outside the study of physiopathogenic hypotheses relating to certain clinical situations, such as mentioned previously. In fact, the provision of a reliable test for estimation of anti-ovary antibodies can have other diagnostic applications and therapeutic applications.

The gonadic system is the most fragile of the endocrine systems. In various polyendocrinopathies, impairment of gonadic function may be the first sign of the illness. In the face of irregularities in the menstrual cycle, an investigation of the anti-ovary antibodies can be the first sign of an incipient autoimmune ovaritis.

Two other groups of pathology are directly concerned by this type of investigation. These are the group of early menopauses and the group of ovarian dystrophies.

These groups are very heterogeneous in their mechanisms and the detection and/or quantification of anti-SEQ ID NO:1 antibodies makes it possible to identify more homogeneous subgroups with possible therapeutic implications.

In the sterility field, patients suffering from so-called "idiopathic" sterility can benefit from this type of analysis, in the same way as the search for other autoantibodies.

Endometriosis, a disease whose mechanisms are still unknown today, obviously occurs in patients in this particular field. Many autoantibodies have been identified in patients suffering from this disease. The mechanism of the sterility is not always clear in these patients. The search for anti-peptide SEQ ID NO: 1 antibodies is of great interest here both on the physiopathological level and on the therapeutic level.

Indeed, the search for such autoantibodies can also have direct therapeutic implications.

Figure 2:
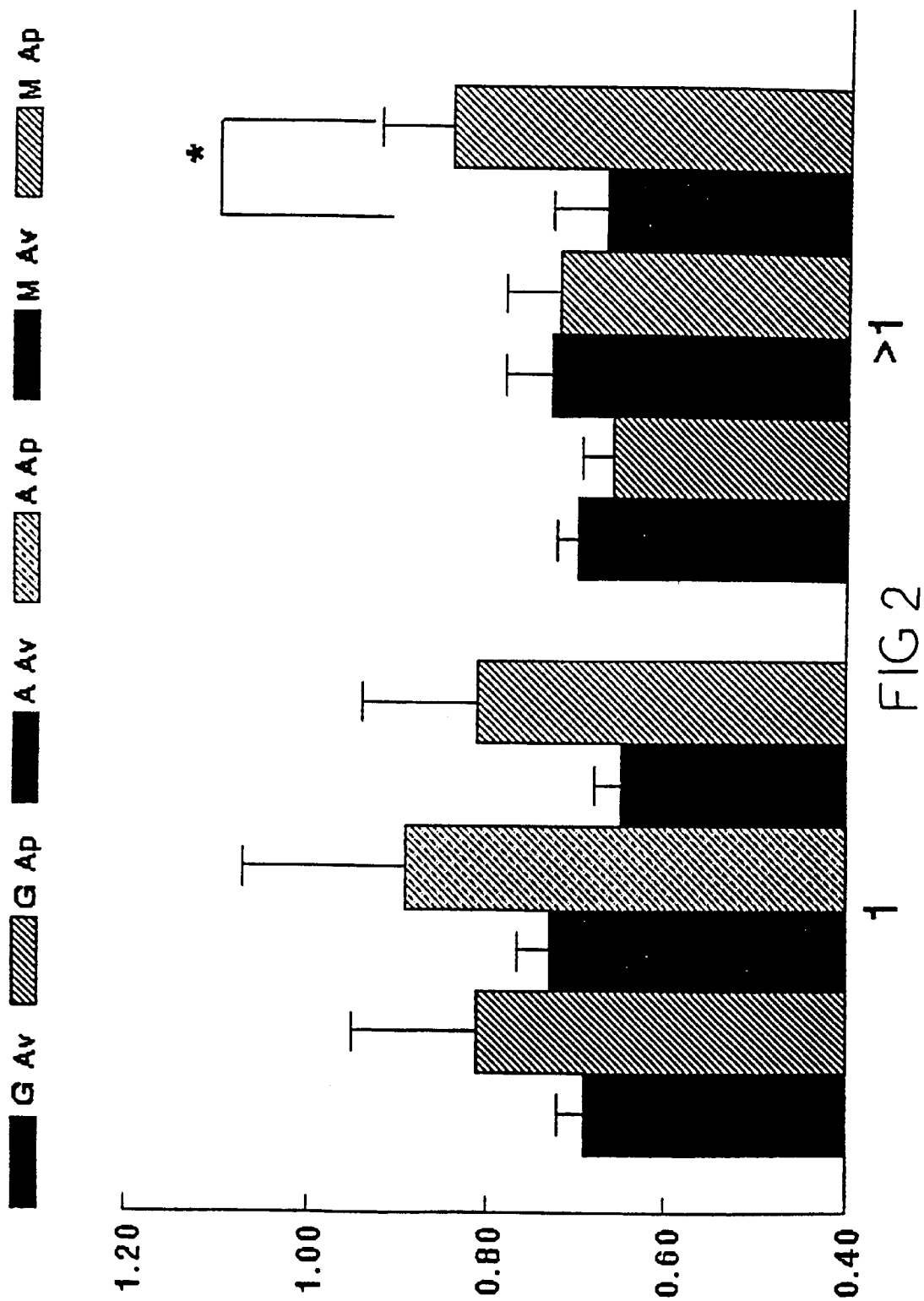

The characteristics and advantages of the objects of the present invention will be evident from the following Examples 1 to 4, supported by FIGS. 1 to 4, among which:

FIG. 1 shows the increase in the levels of anti-peptide SEQ ID NO: 1 antibodies, FIG. 2 shows the increase in the levels of anti-peptide SEQ ID NO: 1 antibodies, after the first IVF attempt and the increase in the IgM SEQ ID NO: 1 after the subsequent IVF attempts, FIG. 3 shows a comparison of the change in the anti-ovary antibodies and anti-peptide SEQ ID NO: 1, before and after puncture in a population of women suffering from tubal sterility, and FIG. 4 demonstrates the higher levels of anti-peptide SEQ ID NO: 1 antibodies, in the absence of biological pregnancy measured from the increase in the levels of HCG (solid columns).

EXAMPLE 1

Immunoenzymatic Technique for Estimation of Anti-ovary Antibodies a) Reagents
   Antigen:
      Ovary
      Corpus luteum
      FSH (Metrodine®, Serono, Levallois-Perret, France)
      Peptides SEQ ID Nos: 1 to 5
   Carbonate-bicarbonate buffer 0.1 M, pH 9.6
   Phosphate buffer saline (PBS) 0.001 M, pH 7.4 (PBS)
   Tween 20 (Sigma, St Louis, Mo., USA)
   Gloria powdered skimmed milk
   Bovine serum albumin (BSA) (Sigma)
   Peroxidase-conjugated anti-human immunoglobulins (IgG, IgA, IgM) (Miles, Napperville, Mass., USA)
   Phosphate-citric acid buffer 0.1 M, pH 5.5
   30 volume hydrogen peroxide (Gifrer Barbezat, Décines, France)
   Ortho-phenylenediamine (OPD) (Sigma)
   2 N sulfuric acid (Prolabo, Paris, France)
b) Apparatus
   Maxisorp plates (Nunc, Roskilde, Denmark)
   Precision balance (Sartorius, Osi, Paris, France)
   Multiskan II spectrophotometer, equipped with a 492 nm filter (Flow laboratories, Helsinki, Finland)
   Titersoft software (Flow Laboratories)
c) Method The concentration of molecules to be adsorbed was determined by checkerboard experiments for each antigen. It is about 1 µg per well.

The binding of the antigens to the solid phase is performed in one night at +4° C. in the amount of 100 µl per well of the solution of antigen in carbonate-bicarbonate buffer. The plate is emptied. The sites of the solid phase still unoccupied are saturated on incubation for one hour at 37° C. with 200 µl per well of 5% powdered milk reconstituted in PBS.

The samples to be tested are diluted in PBS to which 0.5% BSA and 0.2% Tween 20 have been added: dilution to 1/50 for the search for anti-ovary and anti-corpus luteum antibodies. The plate is emptied and washed 3 times in PBS. The samples are distributed in the amount of 100 µl per well. The plate is incubated for 45 minutes at 37° C.

The anti-isotypes are diluted in the same solution that was used for the dilution of the samples:

1/10,000 for the anti-IgGs

1/5000 for the anti-IgAs

1/5000 for the anti-IgMs.

The plate is again emptied and washed 3 times in PBS. Then the anti-isotypes are distributed in the amount of 100 µl per well. The plate is incubated for 45 minutes at 37° C.

The developer solution is prepared on the spot, as follows for one plate:

12 ml of phosphate-citric acid buffer 6 mg of OPD 12 ml of $H_2O_2$.

After 3 further washings of the plate, 100 µl of developer solution are distributed into each well. After appearance of a yellow colour of greater or lesser intensity the reaction is stopped with 50 µl of $H_2SO_4$. The plate is read on the spectrophotometer at 492 nm using the Multiskan II reader.

The results are firstly expressed as optical density (O.D.) then calculated as ratios relative to a control sample at the limit of positivity. Any ratio greater than 1 is considered as positive.

EXAMPLE 2

Selection of Antigenic Peptides

The inventors firstly discovered that FSH, then the peptides consisting of the sequence of amino acids 78–93 and 80–87 of the β-chain of FSH, identified respectively by SEQ ID No.1 and 5, are simultaneously recognized by serums containing anti-ovary antibodies and by 2 anti-β-FSH monoclonal antibodies (property of bioMérieux, 22A3G7; 5H3E8), which have the characteristic of being immunoreactive with metrodine and ovarian extracts, while an anti-β-FSH monoclonal antibody (property of bioMérieux, 7G5A1) only recognizing metrodine does not react with this sequence.

Given that the sequence of amino acids 78–93 of the β-chain of FSH contains 3 cysteines, 4 peptides of 16 amino acids corresponding to the different disulfide bridge possibilities were synthesized.

These four peptides are identified by the respective references SEQ ID NO: 1, SEQ ID NO: 2, SEQ ID NO: 3 and SEQ ID NO: 4, and are described at the end of the specification.

These four peptides obtained in lyophilized form were, after reconstitution and dialysis, used as antigens in a series of ELISA tests on 30 sera from patients.

Moreover, these same sera were tested against the crude ovarian antigens.

The immunoenzymatic technique used is that described in Example 1.

The results of the correlation obtained between the reactivity of the sera toward the ovarian antigen and that of the same sera toward each of the peptides tested, and expressed by an r value, are shown in Table I below:

TABLE I

|  | SEQ ID No.1 | SEQ ID No.2 | SEQ ID No.3 | SEQ ID No.4 |
| --- | --- | --- | --- | --- |
| IgG AOA | 0.74 | 0.44 | 0.79 | 0.59 |
| IgA AOA | 0.46 | 0.28 | 0.49 | 0.49 |
| IgM AOA | 0.81 | 0.75 | 0.71 | 0.69 |

It is found that the best correlation coefficients are obtained for the IgMs on the one hand (which had already been noted with the commercial FSH) and for the peptide SEQ ID NO: 1 on the other hand.

The same results as those obtained for the peptide SEQ ID No.1 were obtained with the peptide SEQ ID No.5, FSH and the β-chain of FSH.

EXAMPLE 3

Antigenicity of the Peptide SEQ ID NO: 1

Two centre and ninety-five sera were tested in duplicate, using the immunoenzymatic method described above, with, firstly, the total ovarian extract, and, secondly, the peptide SEQ ID NO: 1. For each antigen, the three immunoglobulin isotypes IgG, IgA and IgM were studied.

a) Population Studied

The patients included in the study were all scheduled for IVF. Their average age was 32.7±4.2 years. The average duration of the sterility was 4.8±2.8 years.

The aetiology of the sterility which had led the couple to IVF was of tubal origin in 24.9% of the cases, of masculine origin in 18.2% of the cases, of idiopathic origin in 8.6%, due to an ovarian dystrophy (PCO) in 3.8% of the cases, and due to an endometriosis in 2.8% of the cases. In 41.7%, at least two of the above aetiologies were present together, constituting mixed aetiologies.

In 209 cases the serum was collected on the eighth day of the stimulation, and in 84 cases the serum was collected 15 days after the puncture.

b) Results

The results of the correlation obtained between the reactivity of the sera toward the crude ovarian antigen and that of the same sera toward the peptide SEQ ID NO:1 tested, and expressed by an r value, are shown in Table II below:

TABLE II

|  | IgG SEQ ID No.1 | IgA SEQ ID No.1 | IgM SEQ ID No.1 |
|---|---|---|---|
| IgG AOA | 0.18 | 0.12 | NS |
| IgA AOA | 0.12 | 0.11 | 0.01 |
| IgM AOA | 0.10 | 0.06 | 0.27 |

A correlation is observed between IgG AOA and IgG SEQ ID NO:1 (r=0.18, p=0.002), and between IgM AOA and IgM SEQ ID NO:1 (r=0.27, p<0.00001). On the other hand, no correlation is observed between IgA AOA and IgA SEQ ID NO:1 (r=0.10, p=0.06).

EXAMPLE 4

Applications of the Peptides of the Invention

Whatever the combination of number of IVF attempts made and sterility aetiology, an increase in anti-peptide SEQ ID NO:1 antibodies was observed after puncture, with a statistically significant difference for the IgM SEQ ID NO:1 (p=0.005) (see FIG. 1).

On the basis of the number of IVF attempts made, before and after puncture, and as shown in FIG. 2, the following are observed:

in first IVF attempt patients, an increase in anti-peptide SEQ ID NO:1 antibodies, after the follicular puncture, whatever the isotype considered, in multiply-punctured patients, a decrease in the IgG and IgA SEQ ID NO:1 post-puncture and a very clear and statistically significant increase in the IgM SEQ ID NO:1 (p=0.01).

on the basis of the aetiology of the sterility and before and after puncture.

For the aetiology of tubal origin, included as it serves as a reference for IVF (IgA p=0.04 and IgM p=0.027), an indisputable increase is observed in the AOAs of isotypes A and M, after puncture, but an increase in the anti-peptide SEQ ID NO:1, which is clearer and statistically significant for these same isotypes (see FIG. 3).

On the basis of the number of ovocytes and embryos obtained.

The presence of anti-peptide SEQ ID NO:1 antibodies appears deleterious to the obtention of ovocytes and embryos.

An attempt was made to define a limit threshold depending on the isotype concerned pre-puncture. From 151 measurements (a certain number of attempts did not get as far as the follicular puncture), it was possible to determine this threshold for the IgA SEQ ID NO:1 at 0.75, for the ovocytes (9.4 vs. 11.8 ovocytes), and at 0.60, for the embryos (3.1 vs. 4.9 embryos).

It should be noted that this threshold is lower than that defined for the IgA AOAs (1.7 for the ovocytes and the embryos).

On the basis of the outcome of the attempt The mean levels of anti-peptide SEQ ID NO:1 antibodies were compared in relation to whether the plasma HCG (chorionic gonadotrophin) estimation was positive (biological pregnancy) or negative (absence of implantation).

In accordance with FIG. 4, on average lower antibody levels were found when the HCG was positive.

These results demonstrate that the peptide SEQ ID NO:1 makes it possible sensitively and specifically to detect antibodies displaying variations parallel to those of antibodies directed against the total ovarian extract.

Moreover, follicular puncture stimulates the appearance of anti-peptide SEQ ID NO:1 antibodies, and patients displaying such antibodies in their serum have less chance of securing a pregnancy after IVF.

What is claimed is:

1. An oligopeptide consisting of a peptide sequence selected from the group consisting of SEQ ID NO: 1, SEQ ID NO: 2, SEQ ID NO: 3, SEQ ID NO: 4 and SEQ ID NO: 5.

2. An antigenic compound capable of being recognized by anti-ovary antibodies, said antigenic compound consisting of an oligopeptide selected from the group consisting of SEQ ID NO: 1, SEQ ID NO: 2, SEQ ID NO: 3 and SEQ ID NO: 4.

3. An immunogenic compound capable of inducing the production of anti-ovary antibodies, said immunogenic compound consisting of an oligopeptide selected from the group consisting of SEQ ID NO: 1, SEQ ID NO: 2, SEQ ID NO: 3 and SEQ ID NO: 4.

* * * * *

SEQUENCE LISTING

<160> NUMBER OF SEQ ID NOS: 5

<210> SEQ ID NO 1
<211> LENGTH: 16
<212> TYPE: PRT
<213> ORGANISM: human FSH

<400> SEQUENCE: 1

```
Val Ala Thr Gln Cys His Cys Gly Lys Cys Asp Ser Asp Ser Thr Asp
  1               5                  10                  15

<210> SEQ ID NO 2
<211> LENGTH: 16
<212> TYPE: PRT
<213> ORGANISM: human FSH
<220> FEATURE:
<221> NAME/KEY: DISULFID
<222> LOCATION: (5)..(7)
<223> OTHER INFORMATION: disulfide bond between the cysteine in
      position 5 and the cysteine in position 7

<400> SEQUENCE: 2

Val Ala Thr Gln Cys His Cys Gly Lys Cys Asp Ser Asp Ser Thr Asp
  1               5                  10                  15

<210> SEQ ID NO 3
<211> LENGTH: 16
<212> TYPE: PRT
<213> ORGANISM: human FSH
<220> FEATURE:
<221> NAME/KEY: DISULFID
<222> LOCATION: (5)..(10)
<223> OTHER INFORMATION: disulfide bond between the cysteine in
      position 5 and the cysteine in position 10

<400> SEQUENCE: 3

Val Ala Thr Gln Cys His Cys Gly Lys Cys Asp Ser Asp Ser Thr Asp
  1               5                  10                  15

<210> SEQ ID NO 4
<211> LENGTH: 16
<212> TYPE: PRT
<213> ORGANISM: human FSH
<220> FEATURE:
<221> NAME/KEY: DISULFID
<222> LOCATION: (7)..(10)
<223> OTHER INFORMATION: disulfide bond between the cysteine in
      position 7 and the cysteine in position 10

<400> SEQUENCE: 4

Val Ala Thr Gln Cys His Cys Gly Lys Cys Asp Ser Asp Ser Thr Asp
  1               5                  10                  15

<210> SEQ ID NO 5
<211> LENGTH: 8
<212> TYPE: PRT
<213> ORGANISM: human FSH

<400> SEQUENCE: 5

Thr Gln Cys His Cys Gly Lys Cys
  1               5
```